(12) United States Patent
Maruyama et al.

(10) Patent No.: US 7,381,709 B2
(45) Date of Patent: Jun. 3, 2008

(54) METHOD OF EXPRESSING FOREIGN GENE IN KIDNEY

(75) Inventors: Hiroki Maruyama, Niigata (JP); Jun-ichi Miyazaki, Osaka (JP)

(73) Assignee: Japan Science and Technology Corporation, Kawaguchi-Shi (JP)

( * ) Notice: Subject to any disclaimer, the term of this patent is extended or adjusted under 35 U.S.C. 154(b) by 19 days.

(21) Appl. No.: 10/478,537

(22) PCT Filed: May 24, 2002

(86) PCT No.: PCT/JP02/05067

§ 371 (c)(1), (2), (4) Date: Nov. 24, 2003

(87) PCT Pub. No.: WO02/097087

PCT Pub. Date: Dec. 5, 2002

(65) Prior Publication Data

US 2005/0070014 A1 Mar. 31, 2005

(30) Foreign Application Priority Data

May 25, 2001 (JP) .............................. 2001-157810
Feb. 8, 2002 (JP) .............................. 2002-032230

(51) Int. Cl.
*A61K 48/00* (2006.01)
*C12N 15/00* (2006.01)

(52) U.S. Cl. ........................................ 514/44; 435/455

(58) Field of Classification Search .................. 514/44
See application file for complete search history.

(56) References Cited

FOREIGN PATENT DOCUMENTS

WO 00/50617 8/2000

OTHER PUBLICATIONS

Tomasoni, S. and A. Benigni. Current Gene Therapy 4:115-122, 2004.*
Imaim E et al. Kidney International 65:1551-1555, 2004.*
Hiroki Maruyama et al., "Kidney-Targeted Naked DNA Transfer by Retrograde Renal Vein Injection in Rats", Human Gene Therapy, Feb. 10, 2002, vol. 13, No. 3, pp. 455-468.
Li-Wen Lai et al., "Correction of Renal Tubular Acidosis in Carbonic Anhydrase I I-deficient Mice with Gene Therapy", J. Clin. Invest., 1998, vol. 101, No. 7, pp. 1320-1325.
Alessandra Boletta et al., "Nonviral Gene Delivery to the Rat Kidney with Polyethylenimine", Human Gene Therapy, 1997, vol. 8, No. 10, pp. 1243-1251.
Makoto Arai et al., "In Vivo Transfection of Genes for Renin and Angiotensinogen into the Glomerular Cells Induced Phenotypic Change of the Mesangial Cells and Glomerular Sclerosis", Biochemical and Biophysical Research Communications, 1995, vol. 206, No. 2, pp. 525-532.
Yoshitaka Isaka et al., "Glomerulosclerosis Induced by In Vivo Transfection of Transforming Growth Factor-β or Platelet-Derived Growth Factor Gene in the Rat Kidney", J. Clin. Invest., 1993, vol. 92, pp. 2597-2601.
Naruya Tomita et al., "Direct In Vivo Gene Introduction into Rat Kidney", Biochemical and Biophysical Research Communications, 1992, vol. 186, No. 1, pp. 129-134.

* cited by examiner

*Primary Examiner*—Peter Paras, Jr.
*Assistant Examiner*—Marcia S Noble
(74) *Attorney, Agent, or Firm*—Wenderoth, Lind and Ponack, L.L.P.

(57) ABSTRACT

The invention of this application provides a method of expressing a gene, which comprises transferring a plasmid vector recombined with an exogenous gene into the kidney by administration via the renal vein so that the exogenous gene is expressed mainly in renal interstitial fibroblasts. The method of this invention can transfer the exogenous gene into the kidneys safely and efficiently and express the transgene over a long period of time.

2 Claims, 12 Drawing Sheets a b c

METHOD OF EXPRESSING FOREIGN GENE IN KIDNEY

This application is a U.S. national stage of International Application No. PCT/JP02/05067 filed May 24, 2002.

TECHNICAL FIELD

The invention of this application relates to a method of expressing an exogenous gene in the kidney. More specifically, the invention of this application relates to a novel method of expressing a gene, in which transfer of an exogenous gene and long-term expression thereof are permitted in order to in vivo or ex vivo gene therapy of renal diseases and the like.

BACKGROUND ART

Kidney-targeted gene transfer has the potential to be one of the most important tools for broadening the understanding of renal disease processes of genetic renal diseases, glomerulonephritis, diabetic nephropathy, acute and chronic renal failure, renal graft and the like, or for revolutionizing treatments of these renal diseases.

Although various methods for kidney-targeted transfer of a gene and an expression thereof have been so far reported, the amount of expressed protein and duration of the expression have been insufficient for a therapeutic use (Gene Ther. 4, 426-431, 1997; J. Clin. Invest. 101, 1320-1325, 1998; Kidney Int. 57, 1973-1980, 2000; Hum. Gene Ther. 8, 1243-1251, 1997; Gene Ther. 7, 279-285, 2000; Biochem. Biophys. Res. Commun. 186, 129-34, 1992; J. Clin. Invest. 92, 2597-2601, 1993; Biochem. Biophys. Res. Commun. 206, 525-532, 1995).

Further, as a vector for transferring an exogenous gene (therapeutic gene), viral vectors (adenovirus vector, herpesvirus vector and the like) are mainly used in view of the transfer efficiency. The use of these viral vectors are however still problematic in securing safety, excluding antigenicity and the like.

Moreover, regarding a sort of nonviral vector, methods of improving the transfer efficiency using synthetic polymers, such as a complex with a cationic liposome (lipoplex) and a complex with a cationic polymer (polyplex), have been also proposed. However, in case of using these synthetic polymers as a vector, it must be concerned with a problem such as disorder of an immune system resulted from the adjuvant function thereof.

Meanwhile, a method has been proposed, in which a recombinant plasmid vector is directly injected into the skeletal muscle, skin or cardiac muscle of mammals and a protein or a peptide is produced in vivo by expression of the gene that is encoding thereof and incorporated in the plasmid vector. This method is based on interesting characteristics of plasmid DNA (naked DNA) reported by Wolff et al. That is, Wolff et al. have reported that; when a plasmid vector recombined with genes encoding various enzymes ($\beta$-galactosidase, luciferase and the like) was directly injected into the muscle of mammals, the recombinant plasmid DNA kept its existence as an episome (extrachromosomal element) in the muscle cells over a long period of time (for several months) without being replicated or incorporated into a host genome, and it was observed in the meantime that those enzymes encoded by insert genes was continuously expressed (Science, 247:1465-1468, 1990). Since then, the gene transfer and expression method by intramuscular injection of this plasmid vector has been expected to be a main stream of future gene therapy that replaces the recombinant viral vector or the like, and its application range has been variously studied. For example, a method had been developed, in which an antigen is expressed in muscle cells by means of intramuscularly injection of a plasmid vector with an incorporated DNA fragment encoding the antigenic protein, and immunological resistance of host is acquired stimulation of the antigen-specific immune response therein. This method is named "DNA vaccine", and excellent in cost and safety in comparison with ordinary inactivated or attenuated virus vaccines. Thus, it attracts much interest as a vaccine in the next generation. In addition to the use as a DNA vaccine for acquiring an immunological resistance, a method of directly transferring the recombinant plasmid vector was shown to be effective for controlling a systemic function with a physiologically active substance or the like. For example, it was reported that a recombinant plasmid vector encoding cytokines (IL-2, IL-4, TGF$\beta$1) was intramuscularly injected into mice, whereby the cytokines expressed in the muscle cells was subjected to systemic circulation and function systemically (Pro. Natl. Acad. Sci. USA, 93:10876-10880, 1996). Incidentally, one of the inventors of this application invented a method using electroporation as an effective approach to transfer a recombinant plasmid vector into cells, and the invention has already been applied for patent (official gazette of JP-A-2000-004715).

As mentioned above, the gene transfer using the recombinant plasmid vector (naked DNA) has been so far employed as a method of directly transferring a vector into tissue cells such as muscle cells, and has never been taken advantage of as a vector to transfer an exogenous gene into in vivo organs.

This invention aims to provide a novel method that enables long-term expression of a transgene using a recombinant plasmid vector as a kidney-targeted gene transfer vector.

Further, it was known that peritubular capillaries (PTC) of the kidney, which comprise a network of interstitial vessels that connects veins at each cortical level, play a major role in maintaining renal function and hemodynamics [The kidney Vol. 1, 6th edn. (ed. Brenner, B. M.) 277-318, W. B. Saunders, Philadelphia, USA, 2000]. Progressive tubulointerstitial fibrosis, which is accompanied by the loss of PTC or tubules typifies, was known as common symptom in all progressive renal diseases (J. Am. Soc. Nephrol. 7, 2495-2508, 1996). The severity of chronic tubulointerstitial changes, rather than that of glomerular damage, was strongly related with decline in renal function and long-term prognosis (Lancet. 2, 363-366, 1968; Hum. Pathol. 1, 631-641, 1970; Nephrol. Dial. Transplant, 5, 889-893, 1990; Kidney Blood Press. Res. 19, 191-195, 1996; J. Am. Soc. Nephrol. 9, 231-242, 1998; J. Am. Soc. Nephrol. 11, 47-56, 2000). Moreover, it was known that an endothelium of the PCT is one of the main targets of acute and chronic renal transplant rejection (17. J. Am. Soc. Nephrol. 10, 2208-2214, 1999; Lab. Invest. 80, 815-830, 2000; J. Am. Soc. Nephrol. 12, 574-582, 2001).

Accordingly, the invention of this application more specifically aims to express an exogenous gene in fibroblasts adjacent to the endothelium of PTC over a long period of time.

DISCLOSURE OF INVENTION

As an invention for solving the foregoing problems, this application provides a method of expressing a gene, which comprises transferring a plasmid vector recombined with an exogenous gene into the kidney by administration via the renal vein so that the exogenous gene is expressed mainly in renal interstitial fibroblasts.

In the method of this invention, the preferable embodiment is that the exogenous gene is a gene for therapy of renal diseases. Another preferable embodiment is that the administration via the renal vein is performed through a percutaneous vein catheter.

In the method of this invention, still another preferable embodiment is that the recombinant plasmid is transferred into the kidney nephrectomized from renal cells or human body in a transplantable state.

BEST MODE FOR CARRYING OUT THE INVENTION

Figure 1:
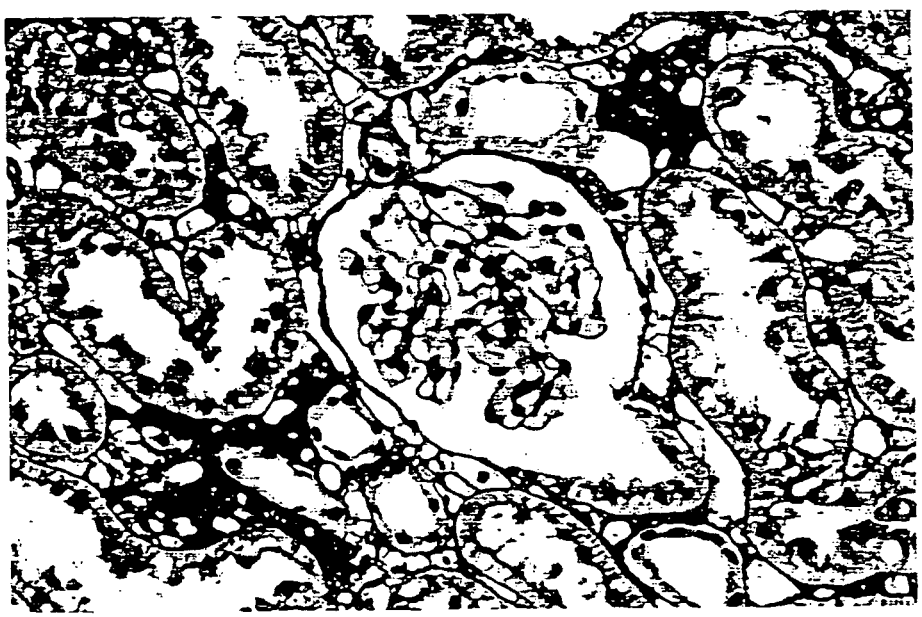
FIG. 1a is a micrograph of a PAS-stained rat kidney section immediately after India ink injection. Magnification is ×350.
FIG. 1b and FIG. 1c are micrographs of serial sections of rat kidneys 1 day after injection with pCAGGS-lacZ stained with X-gal and immunohistochemically stained with an anti-RECA-1 antibody respectively. Magnification is ×260.
Figure 1:
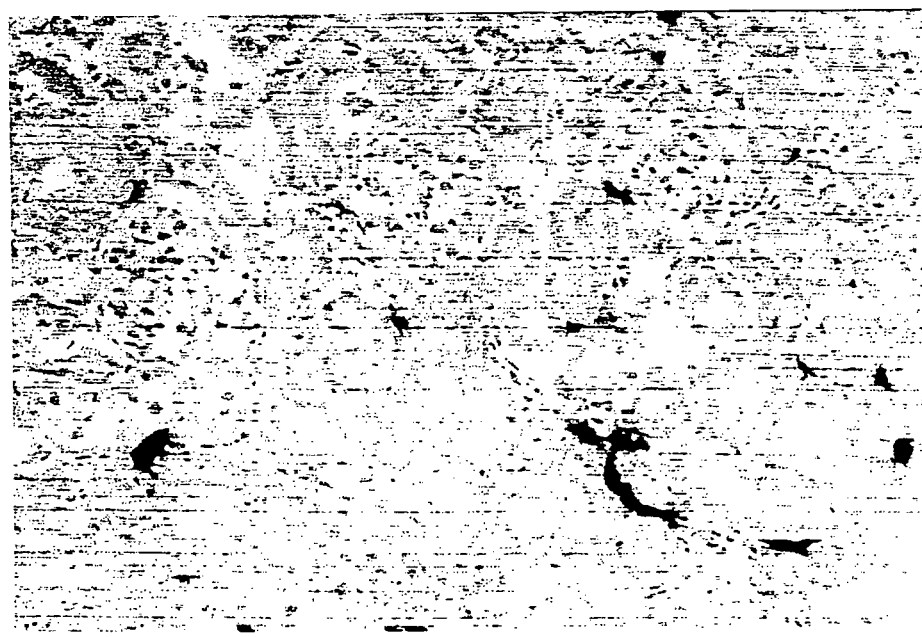
Figure 1:
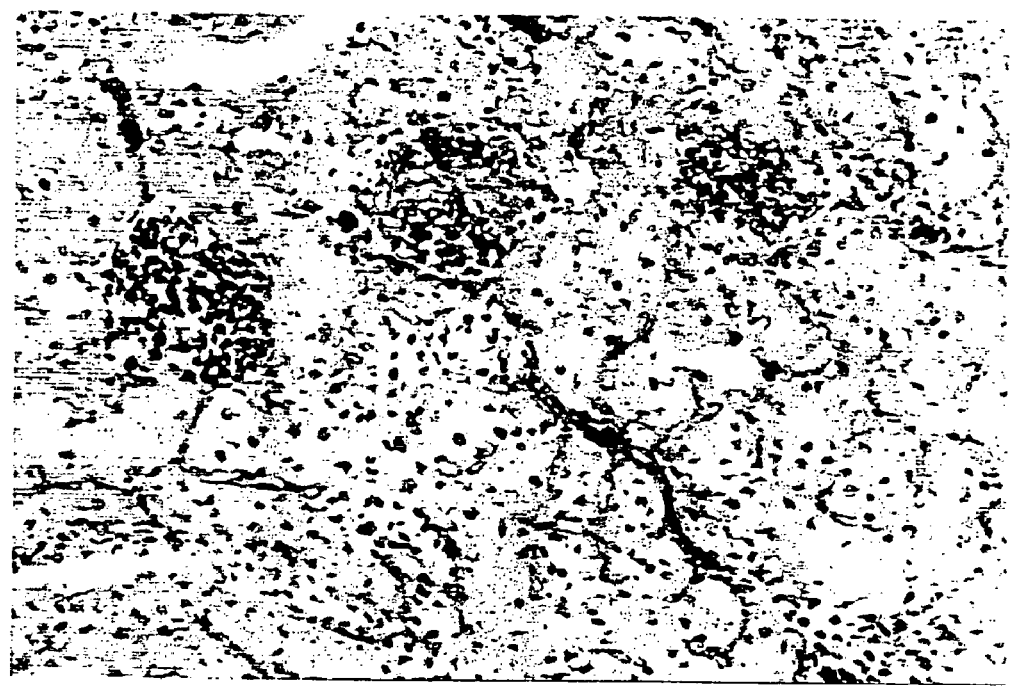

In the method of this invention, an exogenous gene for being incorporated into a plasmid vector includes a gene (polynucleotides such as DNA and RNA), for example, which encodes various cytokines and hormones that influence the kidney function. Further, a therapeutic gene for a renal diseases is also available in accordance with purpose of the method of this invention. Moreover, in the method of this invention, therapeutic genes for other non-renal diseases (for example, α-galactosidase A gene on Fabry disease, and Epo gene on β-thalassemia) can be used. That is, in the method of this invention, a transgene can be expressed in the kidney over a long period of time also by transferring a plasmid vector in a small amount of, for example, 2 μg. Therefore, a treatment of various diseases with supplying a secretory protein, in which the kidney fills a role of gene expression factory (biofactory), will be put into practice.

With respect to such a gene (polynucleotide), a genomic gene can be used as such, or mRNA transcribed from a gene and cDNA synthesized from mRNA can also be used. In case of using mRNA or cDNA, a promoter/enhancer sequence or the like which controls gene expression in the kidney is ligated with a polynucleotide.

The plasmid vector is not particularly limited, and plasmid DNA ordinarily used for animal cell expression can properly be used. The incorporation of an exogenous gene polynucleotide into a plasmid DNA can also be performed by a known method.

The thus-constructed recombinant plasmid vector is retrogradely administered into the kidney via the renal vein. The targeted kidney is a human or non-human mammal kidney. When the human kidney is targeted, an effect as gene therapy is expected. Further, in case of the non-human animal, for example, a renal disease model animal is targeted, whereby the effect of the therapeutic gene transferred can be confirmed at the animal individual level. Alternatively, a novel renal disease animal model can be provided by in vivo expression of a gene, which is responsible for a renal disease.

The transfer of a recombinant plasmid into the kidney can be performed by meas of injecting plasmid solution into temporarily clamped the renal vein, in which the plasmid solution is prepared by mixing an injection liquid with the recombinant plasmid. Or, it is also possible to inject plasmid solution through the catheter that is percutaneous vein catheter inserted in the femoral vein, jugular vein, subclavian vein, cubital vein or the like. The concentration of the plasmid in the injection liquid or the dose of the injection liquid varies according to sort of a targeted animal. In case of humans, the plasmid may be administered at a dose of from 1 µg to 20 mg.

In the kidney, to which the recombinant plasmid vector has been administered by the foregoing method, an exogenous gene incorporated in the vector is expressed for at least 6 months. Accordingly, an improvement of the renal function or a therapeutic effect for a renal disease with a gene is maintained for a long period of time.

The method of this invention can also be applied to a renal tissue nephrectomized from the human body in a transplantable state. In this case as well, the kidney is nephrectomized along with the vein, and the plasmid solution is administered into the kidney through this vein. And the kidney having injected therein the recombinant plasmid vector is transplanted into the human body, whereby the transgene is expressed within the kidney to attain the improvement of the renal function and the effect for renal disease therapy over a long period of time.

EXAMPLE

The invention of this application is illustrated more specifically in detail below by referring to Example. However, the invention of this application is not limited by the following Example.

1. Methods 1.1 Plasmid DNA

Recombinant plasmid vector pCAGGS-Epo was constructed by inserting erythropoietin (Epo) cDNA into an XhoI site of the pCAGGS expression vector that has the CAG (cytomegalovirus enhancer/chicken β-actin hybrid) promoter (Gene, 108, 193-199, 1991). This construction was carried out by a method using Qiagen EndoFree plasmid Giga kit (Qiagen GmbH, Hilden, Germany) described in a literature (Hum. Gene Ther. 11, 429-437, 2000). The empty pCAGGS plasmid without inserting Epo cDNA was used as a control.

1.2 Rats

Eight-week-old male Wistar rats were purchased from Charles-River Japan Inc. (Tokyo, Japan), and were be subjected to gene transfer.

1.3 Injection of Plasmid DNA

The plasmid DNA was diluted in Ringer's solution. The rats were anesthetized with diethyl ether. Immediately after incision of the median section of the abdomen, the plasmid DNA solution was injected, and the left renal vein and artery were clamped. Using a 24-gauge catheter (SURFLO I.V.; Terumo, Tokyo, Japan), the plasmid DNA solution was injected into the vein, and the blood flow was re-established immediately after the injection. Incubation was not performed. Pressure was applied for 5 seconds to allow hemostasis at the injected site.

1.4 Total Tissue DNA Extraction and PCR

On day 1, and 24 weeks after the injection, rats to which 100 µg of pCAGGS-Epo had been administered were sacrificed under general anesthesia, and both kidneys, the brain, heart, lungs, liver, spleen, muscle, skin, testes and blood were harvested. DNA was isolated from the tissue samples according to Laird et al. (Nucleic Acids Res. 19:4293, 1991). The cytomegalovirus (CMV) immediate-early enhancer region contained in pCAGGS-Epo was amplified by PCR using the following specific primers.

```
                                        (SEQ ID No. 1)
CMV-1 forward primer:    5'-GGGTCATTAGTTCATAGCC-3'

(SEQ ID No. 2)
CMV-2 reverse primer:    5'-GGCATATGATACACTTGAT-3'
```

The PCR protocol consisted of [1 min. at 95° C.: 2 min. at 60° C.: 2 min. at 74° C.]×1 cycle and [1 min. at 94° C.: 1 min. at 60° C.: 1 min. at 72° C.]×29 cycles. The PCR products were subjected to 4% agarose gel electrophoresis for analysis of the CMV enhancer DNA of 215 bp.

1.5 Total Tissue RNA Extraction and RT-PCR

On day 1 after the injection, rats to which 100 µg of pCAGGS-Epo or pCAGGS had been administered were sacrificed under general anesthesia, and both kidneys, the brain, heart, lungs, liver, spleen, muscle, skin and testes were harvested. Total RNA was isolated from the tissue samples using Isogen (Nippon Gene, Tokyo, Japan). An expression of Epo mRNA and glyceraldehyde 3-phosphate dehydrogenase (G3PDH) mRNA was detected by RT-PCR using the following specific primers. The analysis of G3PDH mRNA was carried out for control.

```
                                        (SEQ ID No. 3)
Epo reverse primer:      5'-GCCCAGAGGAATCAGTAGCA-3'

(SEQ ID No. 4)
Epo forward primer:      5'-TCTGACTGACCGCGTTACTC-3'

(SEQ ID No. 5)
G3PDH reverse primer:    5'-TCCACCACCCTGTTGCTGTA-3'

(SEQ ID. No. 6)
G3PDH forward primer:    5'-ACCACAGTCCATGCCATCAC-3'
```

The Epo forward primer was designed to hybridize with the sequence immediately downstream of the transcriptional start site of the CAG promoter. That is, the Epo RNA-detecting primer set, that was designed to encompass the intron located between the CAG promoter and the Epo cDNA in pCAGGS-Epo, enabled to distinguish RT-PCR product of the Epo RNA from that of plasmid DNA or genomic DNA. The primer set for detecting G3PDH mRNA was also designed to contain an intron. The RT-PCR products were analyzed by electrophoresis on a 4% agarose gel. The length of the expected products was 170 bp for Epo mRNA and 452 bp for G3PDH mRNA.

1.6 Blood Analyses

Epo levels, hematocrit, reticulocytes and serum creatinine were measured according to a description of a literature (Hum. Gene Ther. 11, 429-437, 2000; Gene Ther. 8, 461-468, 2001).

1.7 X-Gal and Immunohistochemical Staining pCAGGS-lacZ expresses *Escherichia coli* β-galactosidase (Gene, 108, 193-199, 1991). Kidneys injected with 100 µg of pCAGGS-lacZ were analyzed histochemically. The bilateral kidneys for X-gal staining were harvested 1 day after the injection, embedded in Tissue-Tek O.C.T. compound (Sakura Finetechnical Co. Ltd., Tokyo), and frozen in mixture of dry ice and acetone. A serial section (5-µm thick) of the kidneys was prepared by slicing with a cryostat, and placed on glass slides coated with 3-aminopropyltriethoxysilane. The slices were fixed by 1.5% glutaraldehyde at room temperature for 10 minutes, washed three times in cold phosphate-buffered saline (5 min./wash), and incubated in X-gal staining solution containing 1 mg/ml X-gal, 2 mM $MgCl_2$, 5 mM $K_4Fe(CN)_6$, 5 mM $K_3Fe(CN)_6$ and 0.5% Nonidet P-40 (pH 7.4) at 37° C. for 3 hours. The slices were stained with X-gal according to a method described in a literature (Nature Biothechnol. 16, 867-870, 1998) and subjected to nuclear stain with nuclear fast red.

To identify the vascular endothelium of the kidney, serial sections were immunostained using Envion+mouse (Dako, Tokyo, Japan) with mouse anti-rat endothelial cell monoclonal antibody RECA-1 (Cosmobio, Tokyo, Japan)(Lab. Invest. 66, 459-466, 1992), and subjected to nuclear stain with hematoxylin.

1.8 Double Antibody Immunofluorescence Staining

To locate the expression site of transgene in PTC, kidneys injected with 100 μg of pCAGGS-lacZ were analyzed. The kidneys at 1 day after injection were sectioned at a 5-μm thickness. The sections were fixed in acetone for 5 minutes at 4° C., and incubated with rabbit anti-*E. coli* β-galactosidase antibody (1:200 dilution, Biogenesis, Poole, UK) and the mouse anti-rat endothelial cell monoclonal antibody RECA-1 (1:100 dilution, Cosmobio) for 30 minutes at room temperature. And then, following incubation was carried out with either fluorescein isothiocyanate (FITC) conjugated swine anti-rabbit IgG (1:20 dilution, DAKO) or tetramethyl rhodamine isothiocyanate (TRITC) conjugated goat anti-mouse IgG (1:20 dilution, Southern Biotechnology Associates, AL, USA), for 30 minutes at room temperature. The sections were examined using BX50 system microscope (Olympus Promerketing, Tokyo, Japan). All micrographs were obtained using PM-30 photomicrography system (Olympus Promarketing), and the pictures were taken using filter setting for FITC and TRITC. Adobe Photoshop (Adobe Systems, CA) was used for image handling. The transgene sites were detected as green fluorescence, and the PTC as red fluorescence.

1.9 Immunoelectron Microscopy

To further determine transgene-expressing site in the PTC on microstructural scale, the kidney injected with 100 μg of pCAGGS-lacZ was analyzed. One day after the injection, rats were placed under general anesthesia with diethyl ether, and perfused through the aorta with 50 ml of PBS followed by 50 ml of periodate-lysine-paraformaldehyde. The kidneys were further fixed with periodate-lysine-paraformaldehyde fixative for 4 hours at 4° C., treated with 1% sucrose in PBS for 1 hour, embedded in Tissue-Tek O.C.T. compound, and frozen in hexane at −80° C. Sections were prepared by slicing with a cryostat to a thickness of 4 μm, and incubated with rabbit anti-*E. coli* β-galactosidase antibody (1:800 dilution, Biogenesis) for 30 minutes at room temperature. After washing in PBS, the sections were incubated with the goat anti-rabbit Ig EnVision+Peroxidase Rabbit antibody (1:10 dilution, DAKO) for 1 hour. The sections were then washed in PBS and incubated with 0.02% diaminobenzidine (DAB) in Tris buffer (pH 7.6) containing 0.01% $H_2O_2$ for 3 minutes. After washing in PBS, the sections were fixed by 2.5% glutaraldehyde for 3 minutes at room temperature. The sections were washed in PBS, further fixed with 1% $OSO_4$ in 0.1 M phosphate buffer (pH 7.2) for 3 minutes, washed in distilled water, dehydrated by ethanol in a phased manner, and flat-embedded in Epok 812 (Oken, Tokyo, Japan), which is equivalent compound to Epon. After polymerization of the Epok 812, the sections were examined by light microscopy. The selected fields were cut with an ultramicrotome to a thickness of 100 nm, and then DAB stained sites of it were analyzed by an H-600 electron microscope (Hitachi, Ibaragi, Japan).

1.10 Renal Histological Analysis

The kidneys were harvested on days 1 and 7, and 24 weeks after the plasmid DNA injection, fixed in 10% buffered formaldehyde, embedded in paraffin, and processed for routine light microscopy. Then, 5-μm sections were stained with periodic acid-Schiff (PAS) for detection of possible tissue damages due to the gene transfer process.

1.11 Kidney Function

One of the side effects of recombinant human Epo therapy is a decline in renal function in uremic rats (Proc. Natl. Acad. Sci. USA, 85:142-146, 1988). An injury of renal function in uremic rats is enhanced by electroporation-mediated Epo gene transfer into muscle (Gene Ther. 8:46 1-468, 2001). It is an expected reason why polycythemia induced by the Epo gene transfer causes adverse effects on the function of gene-transferred kidney. Therefore, it was examined whether the kidney could function normally immediately after the renal vein injection of 1.0 ml of 100 μg pCAGGS (which itself did not influence renal function by transgene expression). In order to prevent the uninjected kidney from compensating for dysfunction of the other injected kidney, the plasmid was injected into the left kidney, and the right one was nephrectomized. Normal rats and uninephrectomized rats without DNA injection served as controls, and the serum creatinine levels as an endogenous marker for kidney function were measured.

1.12 Statistical Analysis

The numerical data were presented as the mean values ± the standard deviation of the mean. All data were analyzed using the StatView statistical program for Macintosh (SAS, Cary, N.C.). The statistical significance was evaluated with the unpaired t test. $P<0.05$ was considered to be statistically significance.

2. Results 2.1 Delivery Site of India Ink

To verify whether plasmid DNA solution could reach the PTC by retrograde renal vein injection, India ink was first injected. It was detected that India ink transferred from the vein to the interstitial area, and it was observed that PTC was enlarged without bleeding (FIG. 1*a*). It was also observed that India ink was transferred into neither the glomerular nor tubular structures.

2.2 Localization of pCAGGS-lacZ Gene Expression

To determine the transgene-expressing site, 100 μg of pCAGGS-lacZ or pCAGGS was delivered into the kidney. Only the kidney interstitium injected with pCAGGS-lacZ was stained with X-gal (FIG. 1*b*), and the kidney injected with pCAGGS was not stained (data not shown). In advance, pCAGGS-lacZ was transferred into 5 rats, and then it was reproducibly confirmed for all of injected kidneys to be stained with X-gal. The endothelium of the PTC and glomerular capillaries reacted with RECA-1 antibody (FIG. 1*c*). Comparison between two serial sections revealed that one was stained with X-gal and the other with RECA-1, and that transgene expression was confined to the interstitium containing PTC.

Figure 2:
FIG. 2 is photographs of double immunostaining of rat kidney sections 1 day after injection with pCAGGS-lacZ. The sections were stained with anti-$E.\ coli$ β-galactosidase antibody (a, green fluorescence), anti-rat endothelial cell antibody (b, red fluorescence), or both antibodies (c, yellow fluorescence).
Figure 2:
Figure 2:
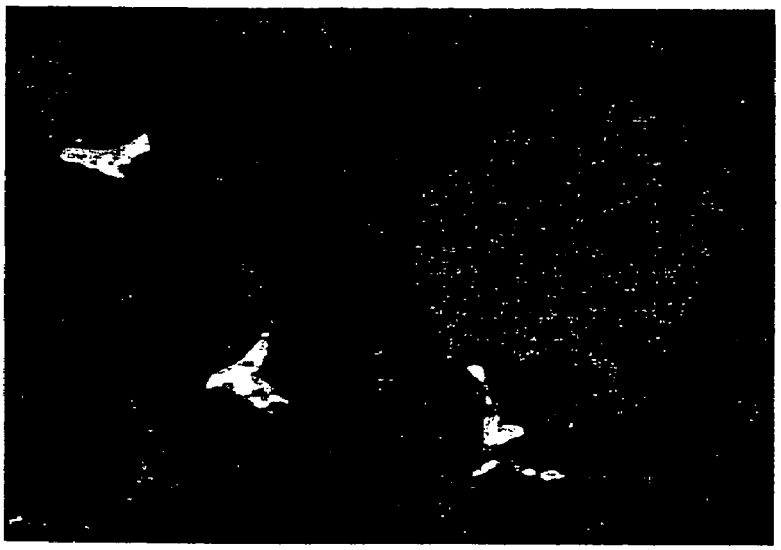

To clarify the transgene-expressing site, the kidney sections were examined by double immunofluorescence staining. The pCAGGS-lacZ expression was detected at sites where several PTC were confluent as broad green fluorescence by immunostaining with a rabbit polyclonal anti-*E. coli* β-galactosidase antibody followed by FITC-conjugated swine anti-rabbit IgG (FIG. 2*a*). PTC endothelial cells were detected as thin red fluorescence by staining with RECA-1 followed by TRITC-conjugated goat anti-mouse IgG (FIG. 2*b*). This double immunostaining showed yellow fluorescence surrounding yellowish green spectrum, suggesting that the transgene was expressed inner or proximity of limited region of the PTC (FIG. 2*c*).

Figure 3:
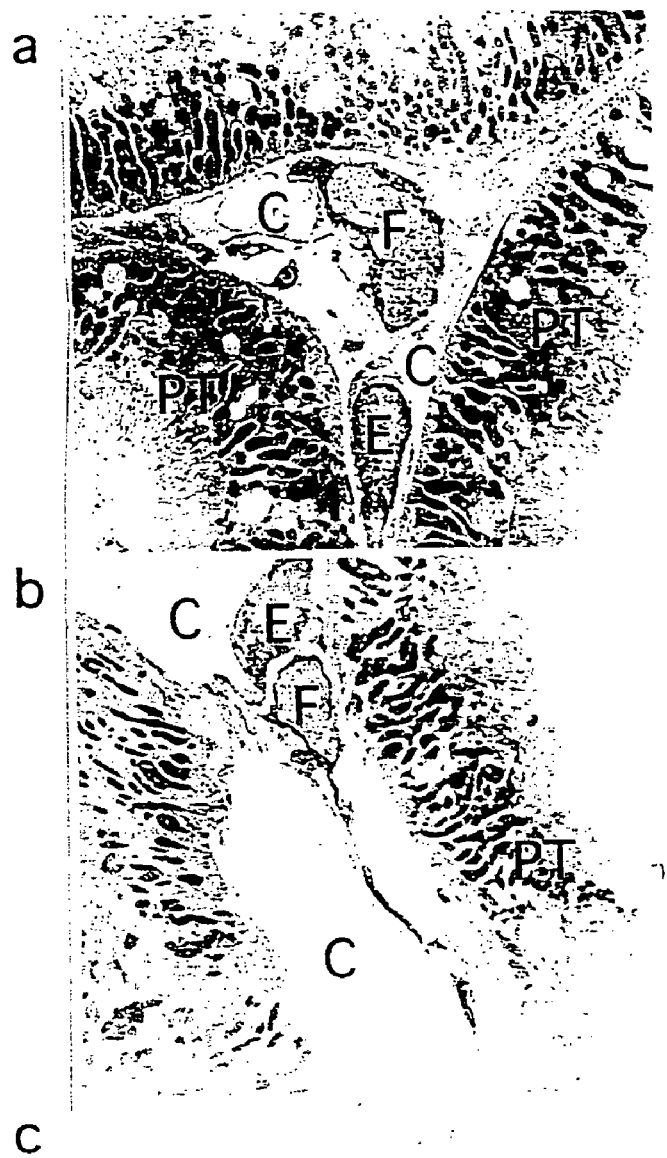
FIG. 3 is photographs of immunoelectron microscopic analysis of ultrathin sections of rat kidneys 1 day after injection with pCAGGS-lacZ. DAB products are distributed throughout the cytoplasm of fibroblasts (a, b, c). The fibroblasts have long cytoplasmic processes and make close contact with the cytoplasm of endothelial cells. The symbol of C indicates capillary lumen; E, endothelial cell; F, fibroblast; PT, proximal tubule. Regarding magnification, a is ×3,200, b×3,000, and c×4,000.

The transgene-expressing cells were further examined by immunoelectron microscopy (FIG. 3), and identified, based on the morphology of renal interstitial cells (Anat. Embryol. 193:303-318, 1996). As a result, the DAB products were detected exclusively throughout the cytoplasm of the fibroblasts adjacent to the PTC (FIG. 3*a, b, c*). The fibroblasts extended long cytoplasmic processes and made close contact with the cytoplasm of the PTC endothelial cells and the tubules (FIG. 3*a, b, c*). No evidence of the DAB products was observed in among the endothelium, macrophages, dendritic cells or pericytes.

The foregoing results show that the transgene-expressing site was the fibroblasts adjacent to the PTC.

2.3 Effects of Injection Parameters on Gene Transfer Efficiency

The physiological effects of the transgene (Epo) were examined by serum Epo measurement and red blood cell analysis immediately after the injection of plasmid vector pCAGGS-Epo.

Figure 4:
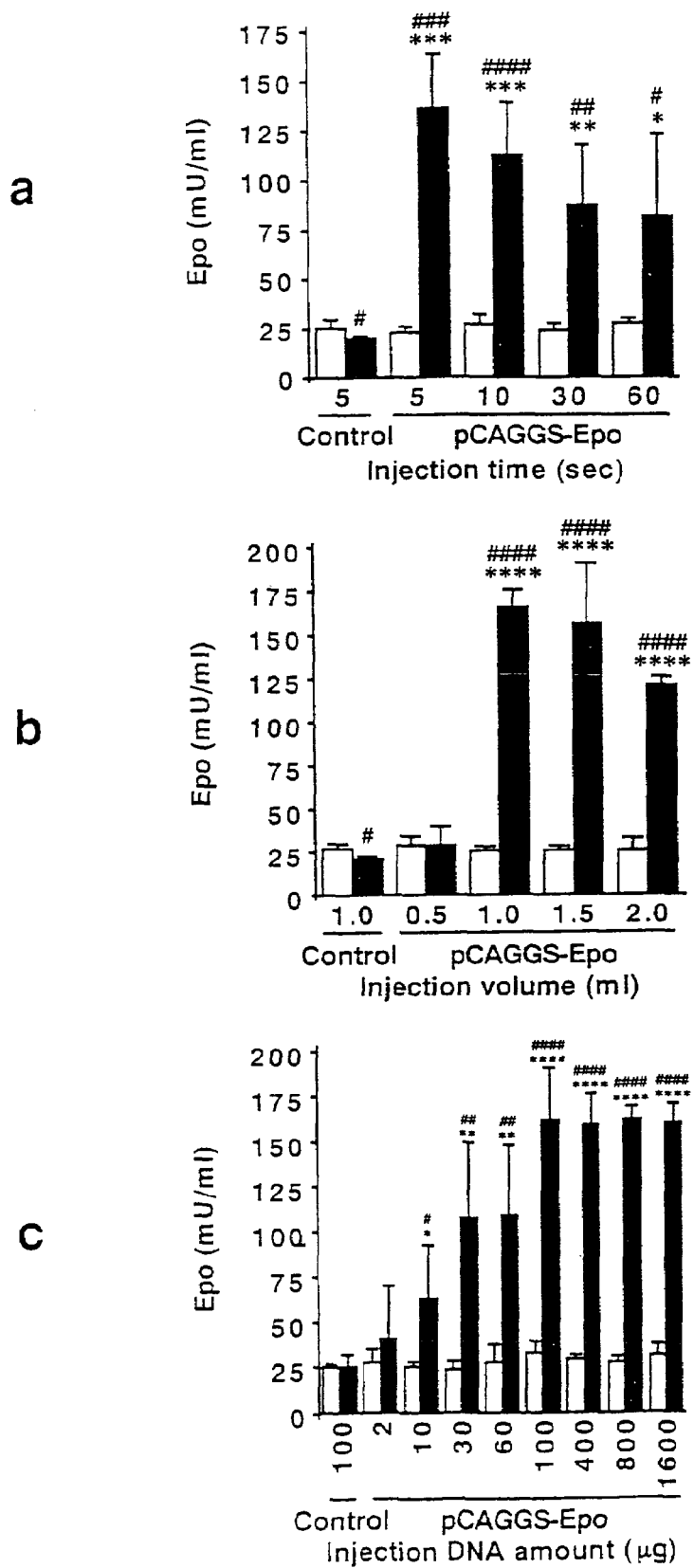
FIG. 4 is graphs showing the effect of injection parameters on Epo levels. Serum Epo was measured 1 week before (□) and 1 week after (■) plasmid DNA injection. The symbols of "a" and "b" represents the effect of injection time (a) or volume (b) on serum Epo levels using 800 μg of pCAGGS-Epo or pCAGGS(n=4/group). Symbolic "c" is the effect of varying the amount of DNA injected on serum Epo levels (n=5/group). Descriptions are as follows: *, $P<0.05$, , $P<0.01$, *, $P<0.001$, and ****, $P<0.0001$ for comparisons with control rats at each time point; #, $P<0.05$, ##, $P<0.01$, ###, $P<0.001$, and ####, $P<0.0001$ for differences between pre- and post-injection within each group.

First, the maximum injection volume acceptable for a rat kidney was measured. The mean kidney capacity of an eight-week-old male Wistar rat was 1.0±0.02 ml (n=10). In several conditions for injection time (varied from 5 to 60 seconds) and volume (varied from 0.5 to 2.0 ml), effects on the gene transfer efficiency were evaluated by measurement of serum Epo levels 1 week before and 1 week after injecting 800 µg of plasmid DNA. Maximal Epo expression was obtained when the plasmid DNA solution was injected within 5 seconds (FIG. 4*a*), and with a volume of 1.0 ml (FIG. 4*b*). During the injection, the kidney showed slight swelling. The effect in varying the amount of DNA was assessed with constant injection time (5 seconds) and volume (1.0 ml). A dose-response correlation was observed between Epo levels and the amount of injected DNA up to 100 µg. Substantial level of Epo gene expression was detected with 10 µg of DNA (FIG. 4*c*).

2.4 PCR Analysis for the Epo Transgene and mRNA in Major Organs

Figure 5:
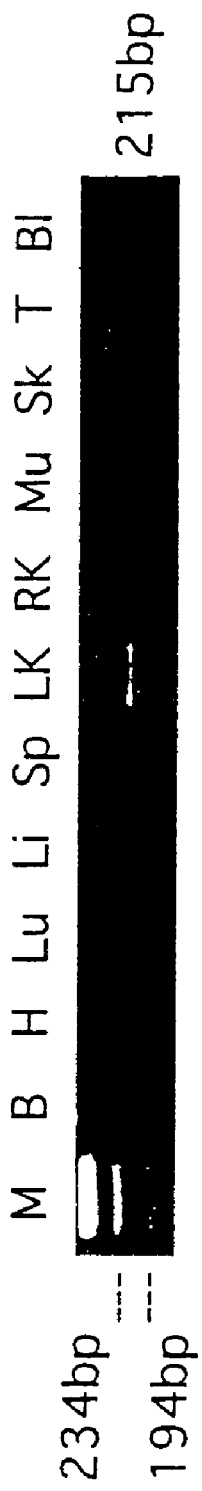
FIG. 5 is results of PCR analysis for pCAGGS-Epo DNA in major organs 1 day after pCAGGS-Epo injection. Descriptions are as follows: B, brain; H, heart; Lu, lung; Li, liver; Sp, spleen; LK, left kidney; RK, right kidney; Mu, muscle; Sk, skin; T, testis; and Bl, blood.
Figure 6:
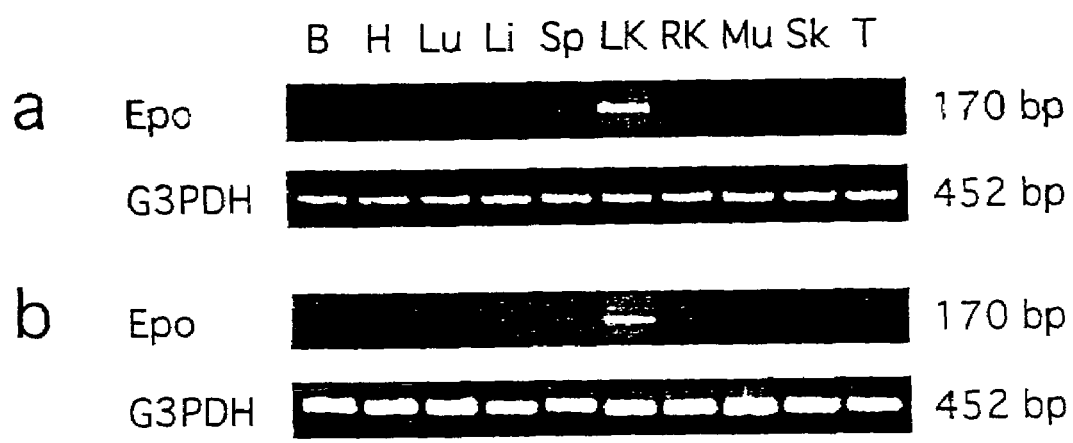
FIG. 6 is results of RT-PCR analysis for Epo mRNA in major organs. Descriptions are as follows: B, brain; H, heart; Lu, lung; Li, liver; Sp, spleen; LK, left kidney; RK, right kidney; Mu, muscle; Sk, skin; T, testis.

Although retrograde injection into the renal vein allows the anatomical targeting of plasmid DNA to the kidney, the injection provides no technical feature ensuring the kidney-specific expression. It is important to examine, therefore, whether the plasmid DNA is transfected into and expressed exclusively in the injected kidney. As shown in FIG. 5, 1 day after injection, Epo DNA was detected by PCR only in the left kidney injected with pCAGGS-Epo, but not in any other tissues. The transgene-derived Epo mRNA was also detected by RT-PCR only in the left kidney injected (FIG. 6*a*), but not in others. The Epo mRNA was not detected in kidneys injected with control pCAGGS (data not shown). However, the control G3PDH mRNA was detected in all the injected kidneys. Likewise, the Epo transgene DNA was detected by PCR (data not shown) and the Epo mRNA, 24 weeks after injection, was also detected by RT-PCR.

From the foregoing results, it was confirmed that the expression of the transgene, injected retrogradely via the renal vein, became specific only to the injected kidney on day 1 after injection and maintained for more than 24 weeks.

2.5 The Time Course after pCAGGS-Epo Injection

The time course of Epo expression was evaluated by varying the amount of DNA injected. The injection liquid volume was set constant as 1.0 ml, and injection time as 5 seconds. Rats were assigned to four groups (3 rats/group): pCAGGS-Epo 100 µg group, pCAGGS-Epo 30 µg group, pCAGGS-Epo 2 µg group, and pCAGGS 100 µg group.

Figure 7:
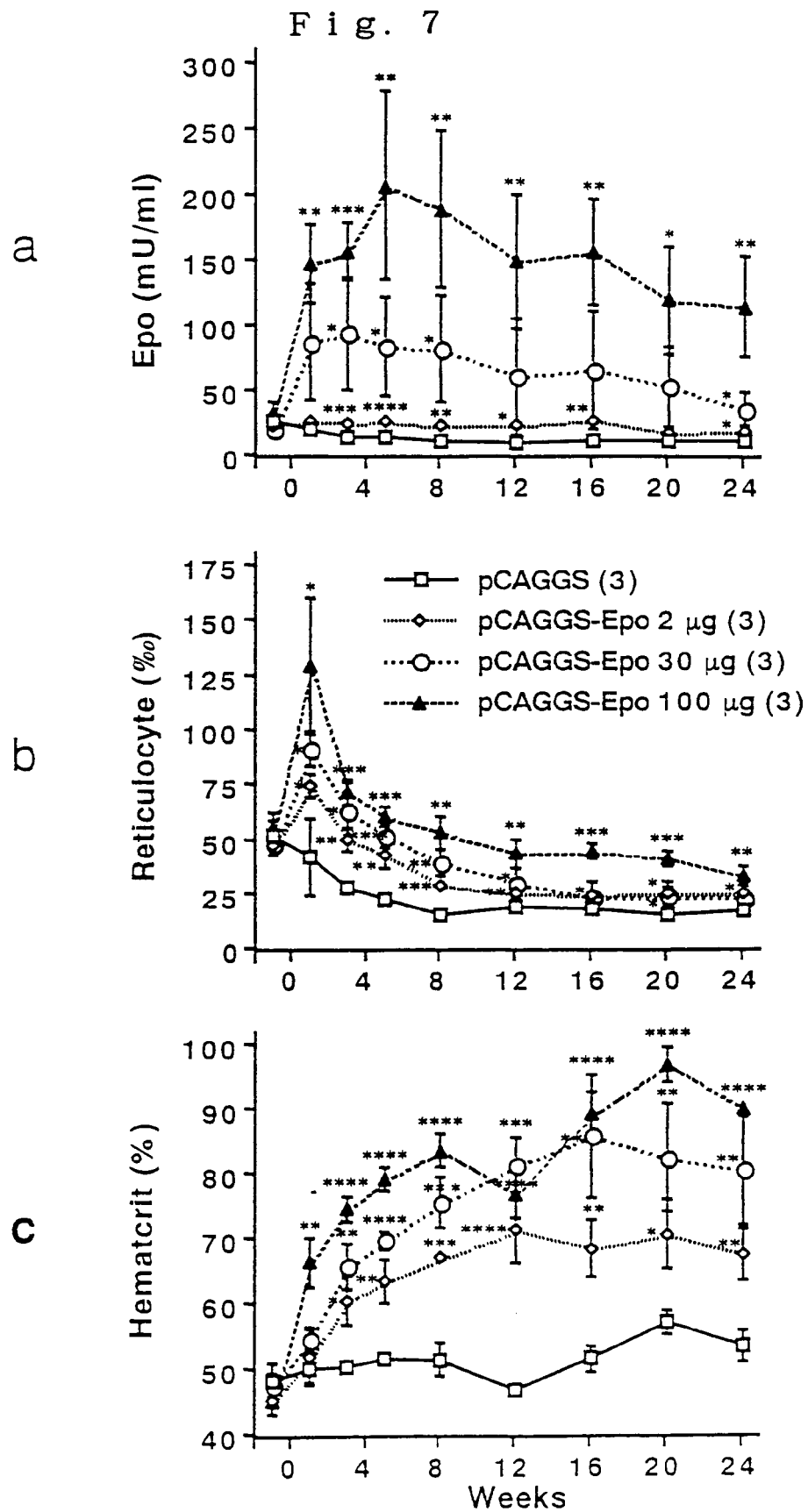
FIG. 7 is graphs showing changes with time of serum Epo levels (a), reticulocyte count (b) and hematocrit (c) after injection of 100 μg plasmid DNA. Descriptions are as follows: *, $P<0.05$, , $P<0.01$, *, $P<0.001$, and ****, $P<0.0001$ for comparison between pCAGGS-Epo and control rats at each time point (n=3/group).

After injection of 100 µg of pCAGGS-Epo, the serum Epo levels peaked at 208.3±71.8 mU/ml at week 5, and gradually decreased to 116.2±38.7 mU/ml at week 24 (FIG. 7*a*). Until week 24, a similar pattern thereof was observed in groups of 2 µg and 30 µg. Transgene-derived Epo secretion caused reticulocytosis (FIG. 7*b*). The hematocrit level was significantly higher in the 2 µg group rats than in the pCAGGS-injected control, after at least 24 weeks, which was the end of examination period (FIG. 7*c*). Since pCAGGS-Epo transfer led to continuous yield of biologically active Epo, both reticulocyte and hematocrit levels were significantly rose in a dose-dependent manner.

2.6 Histological Examination for Kidney Damage

Figure 8:
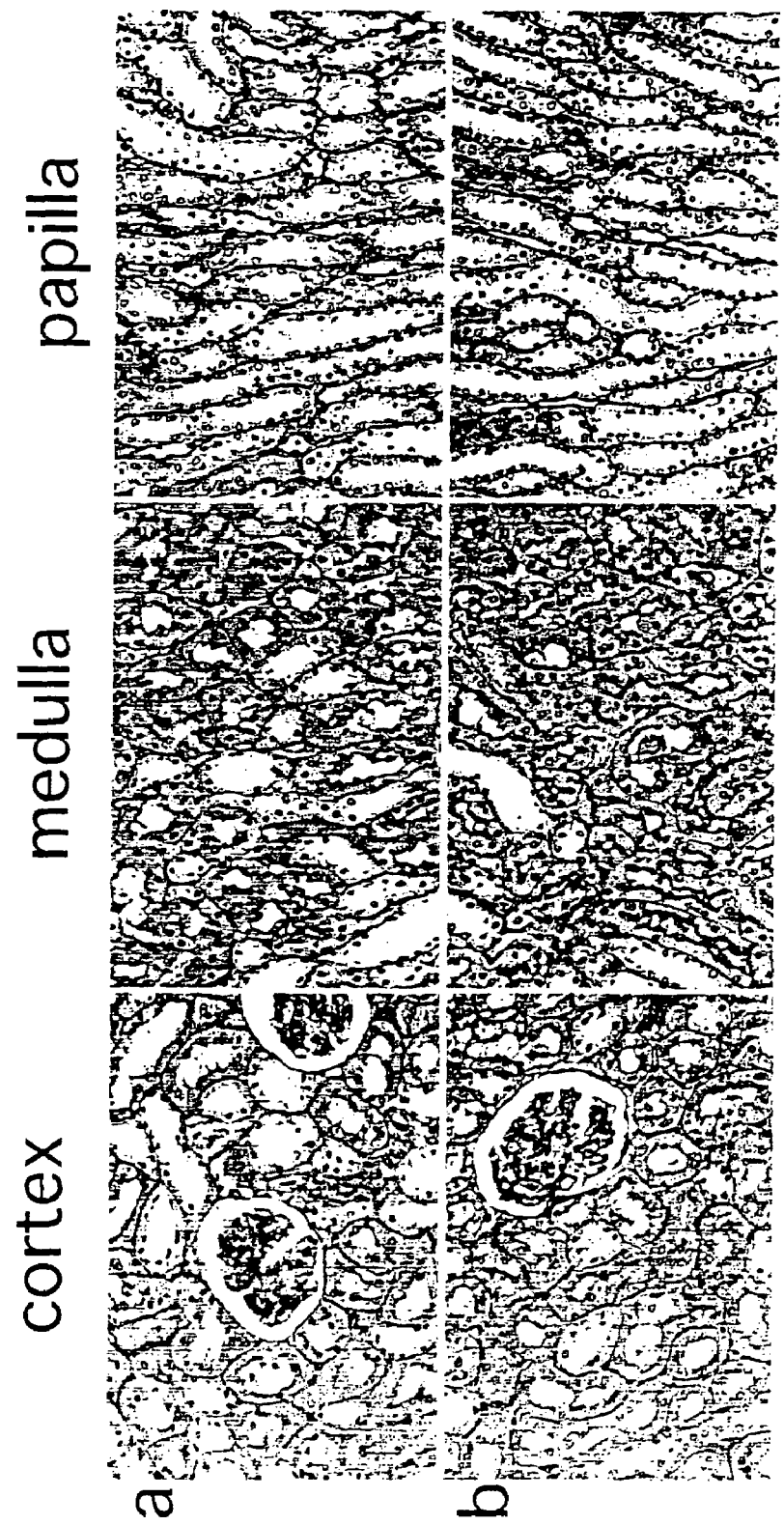
FIG. 8 is micrographs showing the result of histological examination for potential kidney damage due to gene transfer. Kidney sections were stained with PAS. Descriptions are as follows: a, a kidney section of uninjected rat; b and c, kidney sections of rat 1 day (b) and 7 days (c) after pCAGGS-Epo injection. Magnification is ×140.
Figure 8:
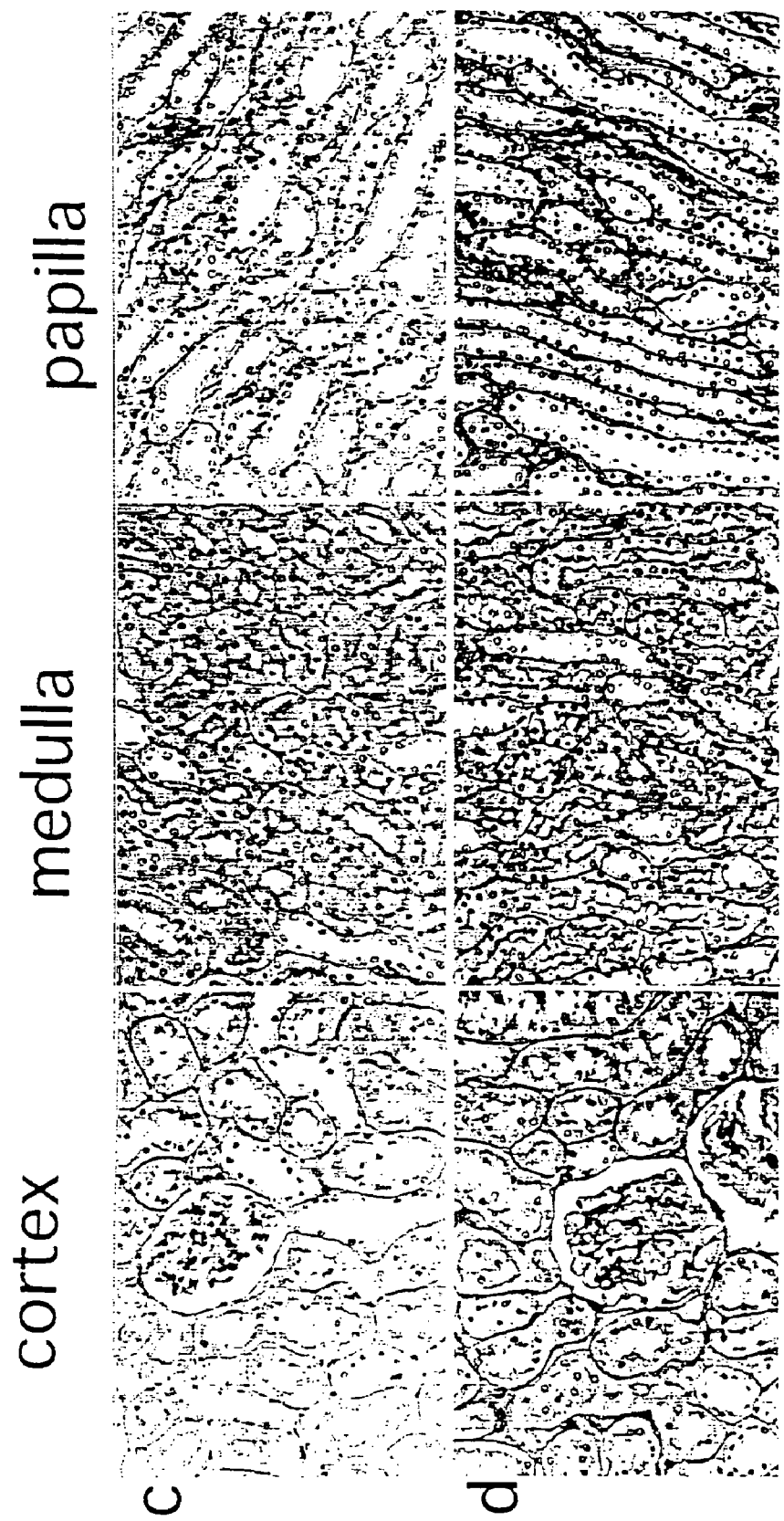

To evaluate the likelihood of kidney damage, kidney sections from rats, which injected with 1.0 ml of Ringer's solution containing plasmid DNA, were analyzed, and compared with normal rats that had not been injected (FIG. 8*a*). In comparison with the kidney sections from normal rats (FIG. 8*a*), it was slightly more difficult to identify the endothelial cells of the PTC in the gene-transferred kidney sections on day 1 (FIG. 8*b*) or day 7 (FIG. 8*c*) after the injection with pCAGGS-Epo. No apparent pathological changes were found in the cortex, medulla or papilla sections obtained on day 1 (FIG. 8*b*) or day 7 (FIG. 8*c*) after the injection with pCAGGS-Epo. Similarly, no apparent pathological changes were found in the rats with an increased hematocrit up to 90% at week 24 after the injection with pCAGGS-Epo.

2.7 Kidney Function after Injection

Figure 9:
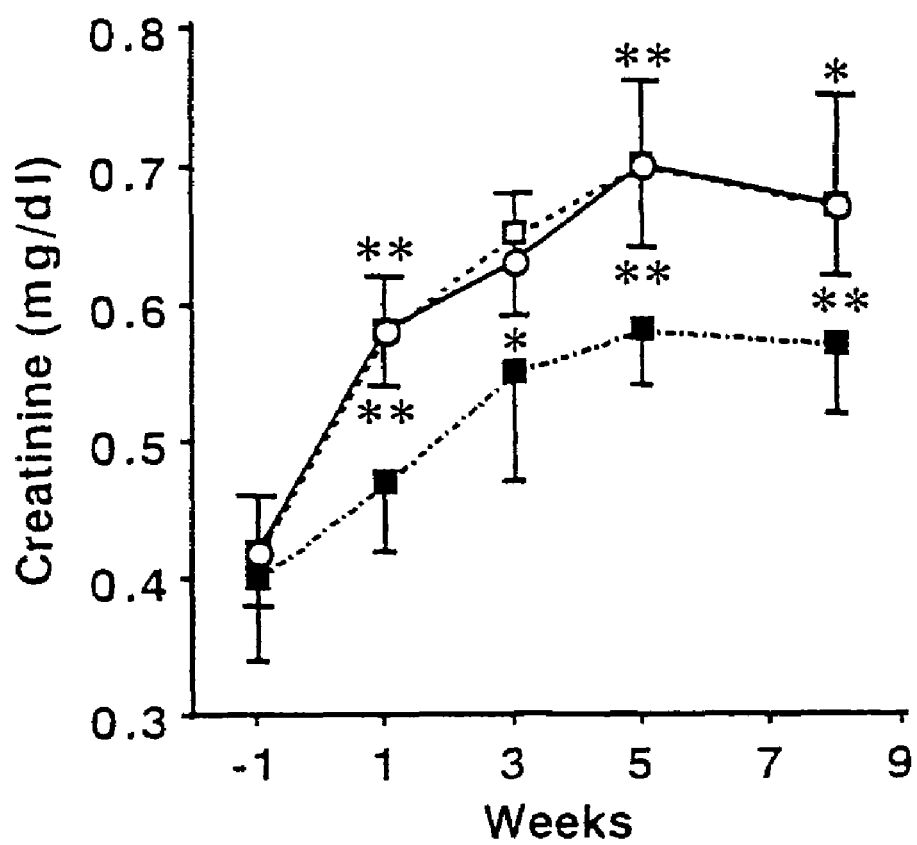
FIG. 9 is a graph showing results of functional analysis of the injected kidney. A open circular symbol (○) designates a uninephrectomized rat with pCAGGS injection, open square (□) indicates a uninephrectomized rat without pCAGGS injection, and closed square (■) shows uninjected and unoperated rat (n=6/group). Other descriptions are as follows: *, $P<0.05$, and **, $P<0.01$ for comparison with normal rats in each time point.

Immediately after the renal vein injection of 1.0 ml of 100 µg pCAGGS, the kidney is normally functional, and not influential on renal function derived from transgene expression. The uninjected kidney might be able to compensate for functional defects and skew interpretation of data. Thus, to examine the function of the injected kidney, it was necessary to remove the uninjected kidney. Therefore, the left kidney was injected, and the right one was nephrectomized. Both normal rats without operation and uninephrectomized rats without DNA injection served as controls. The serum creatinine levels as an endogenous marker for kidney function were measured. Serum creatinine levels increased with growth, and this increase was significantly enhanced by uninephrectomy. The serum creatinine levels were not significantly different between the uninephrectomized groups at any time point, irrespective of DNA injection (FIG. 9). All the rats survived surgery and the injection and appeared normal.

The foregoing results demonstrated that the kidney could function normally after gene transfer thereto via retrograde renal vein injection.

2.8 Kidney Function of Rats at 24 Weeks after pCAGGS-Epo Transfer

The kidney function of rats with an increased hematocrit up to 90% 24 weeks after pCAGGS-Epo transfer was examined. There was no difference in the serum creatinine levels between the pCAGGS-Epo 100 µg group rats and the pCAGGS group rats at week 1 before injection (0.5±0.0 mg/dl versus 0.6±0.1 mg/dl). The serum creatinine level at 24 weeks after injection was significantly higher in the pCAGGS-Epo 100 μg group rats than in the pCAGGS group rats (0.6±0.1 mg/dl versus 0.5±0.1 mg/dl (p<0.05). However, the serum creatinine levels in each group were within normal range.

2.9 Role of the CAG Promoter in Kidney-Targeted Gene Expression

Figure 10:
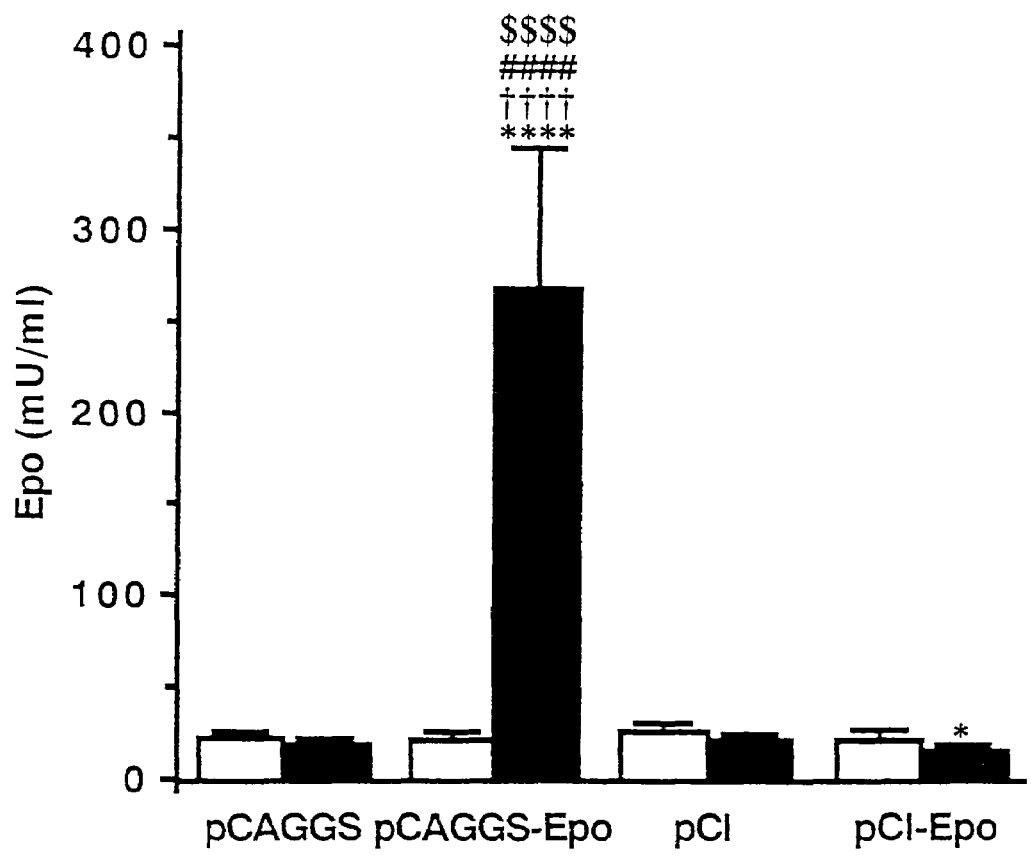
FIG. 10 is results of examining the role of the CAG promoter in kidney-targeted gene expression. Serum Epo level was measured 1 week before (□) and 1 week after (■) naked DNA injection(n=6/group). Other descriptions are as follows: *, $P<0.05$, and ****, $P<0.0001$ for differences between pre- and post-injection Epo levels within each group; ++++, $P<0.0001$ for comparison with pCAGGS group (at each time point); ####, $P<0.0001$ for comparison with pCI group (at each time point); $$$$, $P<0.0001$ for comparison with pCI-Epo group (at each time point).

Expression plasmid vectors containing the CMV promoter/enhancer region have usually been used in kidney-targeted gene transfer experiments (Science 261:209-211, 1993; Hum. Gene Ther. 8:1243-1251, 1997; Gene Ther. 4:426-431, 1997; J. Clin. Invest. 101:1320-1325, 1998; Gene Ther. 7:279-285, 2000). It is therefore important to discriminate between the effect of difference ingene transfer method and that of promoter. Thus, the retrograde renal vein injection method was performed with a CMV-based construct (pCl-Epo). That is, pCAGGS-Epo was digested with restriction enzyme EcoRI and a 726-bp rat Epo cDNA fragment (726 bp) was obtained. The plasmid pCl-Epo was constructed by incorporating the Epo cDNA fragment into an EcoRI site of the pCl expression vector that bears the CMV immediate-early gene enhancer/promoter (Promega, Madison, Wis.), and the plasmid was prepared as described in a literature (Hum. Gene Ther. 11; 429-437, 2000). The pCl plasmid without insert fragment was used as a control. Rats were assigned to four groups (6 rats/group): pCAGGS-Epo 100 μg group, pCAGGS 100 μg group, pCI-Epo 100 μg group, and pCI 100 μg group. The serum Epo levels were measured 1 week before and after respective injection. Epo mRNA was also confirmed in the kidney injected with pCI-Epo by RT-PCR (data not shown). As shown in FIG. 10, however, the serum Epo levels were quite low in case of pCI-Epo group. In another case of pCAGGS-Epo group, high serum Epo levels were shown in contrast.

The foregoing results clearly demonstrated that the CAG promoter was one of the important requirements for the kidney-targeted gene transfer by the retrograde renal vein injection method.

3. Considerations

The foregoing results demonstrated that retrograde renal vein injection of recombinant plasmid vector enabled the long-term expression of exogenous genes to the interstitial fibroblasts adjacent to the PTC.

That is, the transgene-expressing site was confirmed to be the fibroblasts adjacent to the PTC by electron microscopic examination. As shown in FIG. 3b, the fibroblasts were adhered to the PTC endothelial cells. The structure of the interstitial tissue in the rat kidney is already reported (Cell Tissue Res. 264:269-281, 1991; Anat. Embryyol. 193:303-318, 1996). These characteristics of the fibroblasts probably account for the results of the double immunostaining, in which yellowish green areas were observed outside of yellow areas.

The interstitial fibroblast is a site filling the key role in development of nephropathy. The common pathway of many progressive renal diseases is the process of fibrosis, which involves the proliferation of renal fibroblasts and the secretion of extracellular matrix by the fibroblasts (Kidney Int. 39:550-556, 1991). The effective in vivo gene transfer into fibroblasts could be of great significance both for development of fibrosis therapy and for further elucidation of the fundamental biological mechanisms of fibrosis (Nephrol. Dial. Transplant. 14:1615-1617, 1999). Interestingly, the peritubular fibroblasts constitute the major site of endogenous Epo production (J. Histochem. Cytochem. 41:335-341, 1993; Kidney Int. 51:479-482, 1997; Kidney Int. 44:1149-1162, 1993). The present study is the first to demonstrate that the retrograde renal vein injection method can deliver an exogenous Epo gene to the endogenous Epo production site.

In the method of this invention, the retrograde renal vein injection was performed with neither a specific vector nor a special device for gene transfer. The preparation of the plasmid DNA solution is simple, compared with lipoplex or polyplex preparation. Nephrotoxicity attributable to gene transfer detected neither by histological nor by functional examination of the plasmid DNA-injected kidney. The method of this invention does not require flushing the kidney before the DNA injection or during incubation. The duration of ischemia caused by the interruption of blood flow during the injection is shorter than 2 minutes. Likewise, the efficient gene expression into the epithelium that is liable to undergo mechanical stress is to support the safety of the method of this invention.

The critical parameters for efficient transgene expression were the injection volume and the injection speed. The optimal injection volume (1.0 ml) for transgene expression was equal to the kidney capacity. The rapid injection of the DNA solution in the appropriate volume might contribute to the protection of the injection plasmid DNA from DNA degradation caused by serum and cellular nucleases, because the rapid injection results in the direct exposure of the DNA molecules to the PTC endothelium before the DNA is mixed with blood.

It was further confirmed that the choice of the CAG promoter is also instrumental for transgene expression and that the CMV promoter is not suitable for kidney-targeted gene transfer by method of this invention.

Epo gene transfer caused erythropoiesis in a dose-dependent manner. The serum Epo levels following the renal vein injection of 100 μg of pCAGGS-Epo were equal to or higher than those following muscle-targeted gene transfer of 400 μg of pCAGGS-Epo by electroporation (Hum. Gene Ther. 11:429-437, 2000; Gene Ther. 8:461-468, 2001). The serum Epo levels at 24 weeks after renal vein injection of pCAGGS-Epo were still approximately one-half of their peak, and equivalent to those at 5 weeks after muscle-targeted gene transfer (Gene Ther. 8:461-468, 2001). Thus, it was confirmed that both the efficiency of gene transfer and the durability of gene expression by renal vein injection are better than those by muscle injection with in vivo electroporation.

In comparison to previous reports (Gene Ther. 4, 426-431, 1997; J. Clin. Invest. 101, 1320-1325, 1998; Kidney Int. 57, 1973-1980, 2000; Hum. Gene Ther. 8, 1243-1251, 1997; Gene Ther. 7, 279-285, 2000; Biochem. Biophys. Res. Commun. 186, 129-34, 1992; J. Clin. Invest. 92, 2597-2601, 1993; Biochem. Biophys. Res. Commun. 206, 525-532, 1995), the method of this invention enables more long-term gene expression. Although the lifespan of the fibroblasts is unknown, it is considerably long. The localization of the gene transfer to the fibroblasts may be an important factor in the long-term expression. This proves that the method of this invention can overcome the critical problems of kidney gene transfer method by nonviral vectors (namely low transfection efficiency and short-term expression).

Moreover, the method of this invention can easily be applied to human. When the catheter method is put to practical use, therapeutic genes can also be delivered to the kidney noninvasively. The method of this invention is also useful for ex vivo gene transfer during kidney transplantation. Success of transplantation mainly depends on suppression of acute rejection (Transplantation, 55, 752-757, 1993; N. Engl. J. Med. 342, 605-612, 2000). The specific gene transfer adjacent to the PCT is also useful for the long-term delivery of therapeutic proteins that suppress either immune cell function or mediators of inflammatory processes.

Industrial Applicability

As has been thus far described in detail above, the invention of this application provides the method, which can transfer the exogenous gene into the kidneys safely and efficiently and express the transgene over a long period of time. The possibility of gene therapy of renal diseases is thereby greatly increased.

The invention claimed is:

1. A method of expressing an exogeneous gene, which comprises administering into a renal vein through a percutaneous vein catheter a plasmid vector comprising an exogenous gene operably linked to a promoter that results in expression of said exogeneous gene in renal cells, wherein said administering results in delivery of vector to the peritubular papillaries (PCT) of kidney and expression of the exogenous gene product in the renal cells adjacent to the PCT.

2. The method according to claim 1, wherein the exogenous gene product is a protein.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 1
gggtcattag ttcatagcc                                               19

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 2
ggcatatgat acacttgat                                               19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 3
gcccagagga atcagtagca                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 4
tctgactgac cgcgttactc                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 5
```

```
tccaccaccc tgttgctgta                                              20
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Synthesized oligonucleotide

<400> SEQUENCE: 6

```
accacagtcc atgccatcac                                              20
```